United States Patent
Fujiwara

(10) Patent No.: US 8,423,111 B2
(45) Date of Patent: Apr. 16, 2013

(54) PROBE HOLDER MOUNTING DEVICE FOR BIOLOGICAL PHOTOMETRIC DEVICE

(75) Inventor: Michiyuki Fujiwara, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 1418 days.

(21) Appl. No.: 12/065,095

(22) PCT Filed: Aug. 28, 2006

(86) PCT No.: PCT/JP2006/316861
§ 371 (c)(1),
(2), (4) Date: Feb. 28, 2008

(87) PCT Pub. No.: WO2007/026644
PCT Pub. Date: Mar. 8, 2007

(65) Prior Publication Data
US 2009/0262342 A1     Oct. 22, 2009

(30) Foreign Application Priority Data
Aug. 29, 2005 (JP) .................. 2005-247598

(51) Int. Cl.
*A61B 5/1455* (2006.01)

(52) U.S. Cl.
USPC ............... 600/344; 600/310; 600/322

(58) Field of Classification Search ........... 600/309–344
See application file for complete search history.

(56) References Cited

U.S. PATENT DOCUMENTS

| 5,680,857 A | * | 10/1997 | Pelikan et al. ............... 600/323 |
| 2004/0054271 A1 | * | 3/2004 | Maki et al. ..................... 600/341 |
| 2004/0236226 A1 | * | 11/2004 | Maki et al. ..................... 600/473 |

FOREIGN PATENT DOCUMENTS

| JP | 9-28696 | 2/1997 |
| JP | 9-28698 | 2/1997 |
| JP | 2002-291751 | 10/2002 |
| JP | 2002-291751 A | 10/2002 |
| JP | 2003-149137 | 5/2003 |
| JP | 2006-149611 | 6/2006 |
| WO | WO 00/07793 A1 | 10/2000 |

* cited by examiner

*Primary Examiner* — Eric Winakur
*Assistant Examiner* — Marjan Fardanesh
(74) *Attorney, Agent, or Firm* — Antonelli, Terry, Stout & Kraus, LLP.

(57) ABSTRACT

A probe holder mounting device for a biological photometric device includes: a probe holder having a plurality of probe mounting parts to which optical fiber probes are mounted; a band-like mounting device body having a plurality of insertion holes into which the probe mounting parts are to be inserted to fix the probe holder in position by means of the insertion holes; belts whose one ends are respectively connected to both longitudinal ends of the mounting device body and whose other ends are engaged with each other; and an adjusting belt connected to the mounting device body at a position where the probe holder is fixed in position in a lateral direction of the mounting device body.

18 Claims, 6 Drawing Sheets

PROBE HOLDER MOUNTING DEVICE FOR BIOLOGICAL PHOTOMETRIC DEVICE

TECHNICAL FIELD

The present invention relates to a probe holder mounting device for a biological photometric device, which is used when mounting a probe holder of a biological photometric device to a subject.

BACKGROUND ART

In a conventional probe device, a plurality of probes are arranged on a shell portion in a lattice-like fashion. A belt is connected to the shell portion via a strap, and, by wrapping the belt around the chin, the shell portion is mounted to the head. The shell portion is formed of a soft rubber such as silicone rubber so that the shell portion may extend in conformity with the head (see, for example, Patent Document 1).

Patent Document 1: JP 2001-286449 A

DISCLOSURE OF THE INVENTION

Problems to be Solved by the Invention

In the above-described conventional method of mounting the shell portion, the belt is wrapped around the chin, so the subject is subjected to feeling of tightness. Further, fine adjustment of the probe positions is rather difficult to perform, resulting in rather poor reproducibility of the mounting position.

The present invention has been made with a view toward solving the above problems. It is an object of the present invention to provide a probe holder mounting device for a biological photometric device which allows easy mounting to a subject without involving excessive tightness and which allows fine adjustment of probe holder positions.

Means for Solving the Problems

A probe holder mounting device for a biological photometric device according to the present invention includes: a probe holder having a probe mounting part for fixing in position an optical fiber probe; a mounting device body into which the probe mounting part is inserted to fix the probe holder in position; a belt connected to both longitudinal ends of the mounting device body for tightening around the head of a subject; and an adjusting belt connected to a lateral end of the mounting device body and to the probe holder.

BEST MODE FOR CARRYING OUT THE INVENTION

In the following, a preferred embodiment of the present invention will be described with reference to the drawings.

Embodiment 1

Figure 1:
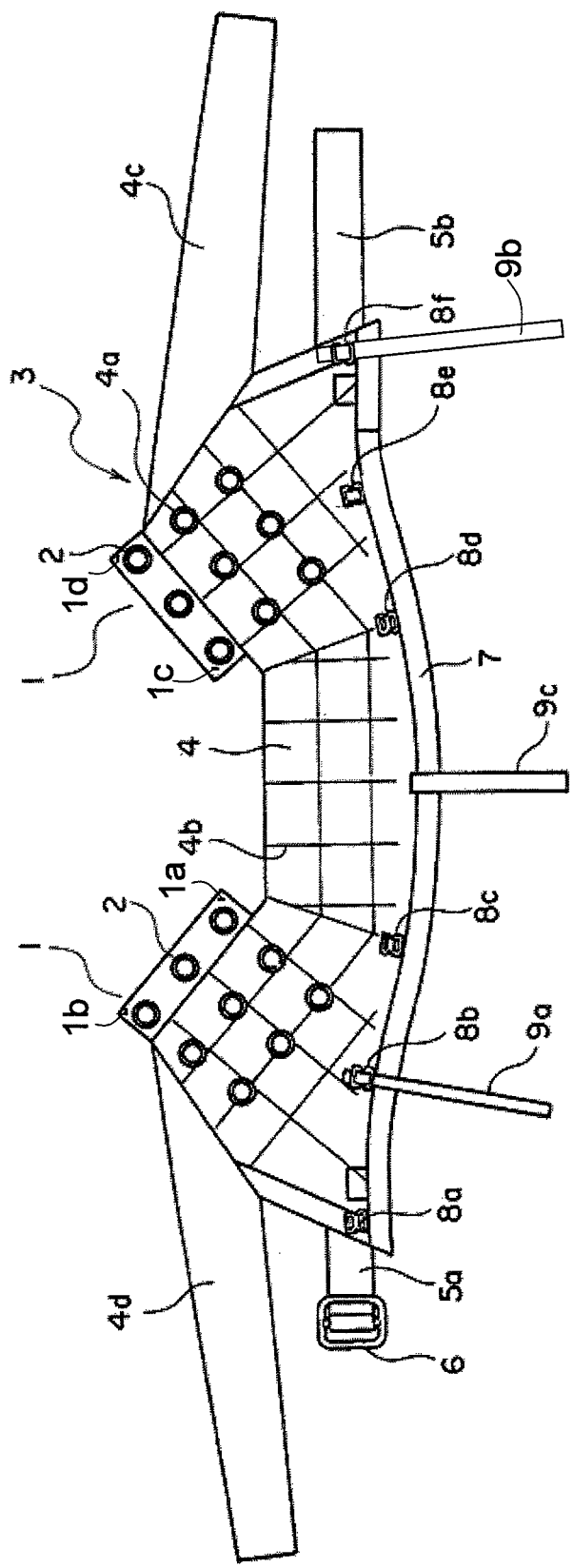
[FIG. 1] A plan view of a probe holder mounting device for a biological photometric device according to Embodiment 1 of the present invention.

FIG. 1 is a plan view of a probe holder mounting device for a biological photometric device according to Embodiment 1 of the present invention with two probe holders 1 mounted thereto. In the figure, each probe holder 1 is equipped with a plurality of probe mounting parts (sockets) 2 to which optical fiber probes are to be mounted. The probe mounting parts 2 are arranged in a matrix-like fashion. The base portions of the probe holders 1 are formed of a flexible material such as silicone rubber.

The probe holders 1 are mounted to the head of the subject by using a probe holder mounting device 3. The probe holder mounting device 3 has a band-like mounting device body 4, belts 5a, 5b respectively connected to both longitudinal ends of the mounting device body 4 and tightening around the head of the subject, a main buckle 6 provided on the one belt 5a serves as a main fastening member, a strap-like core 7 fixed in position so as to extend in the longitudinal direction of the mounting device body 4, a plurality of adjusting strap buckles 8a through 8f mounted at intervals to the mounting device body 4, and a plurality of adjusting straps 9a through 9c connected to the mounting device body 4 either through the intermediation of the adjusting strap buckles 8a through 8f or directly.

The mounting device body 4 is formed of an expandable cloth and is wrapped around the subject when mounting the probe holders 1 to the subject. The mounting device body 4 is provided with a plurality of insertion holes 4a for inserting the probe mounting parts 2 of the probe holders 1. The insertion holes 4a are provided by using a pair of scissors or the like in conformity with the positions of the probe mounting parts 2 of the probe holders 1 used.

As shown in FIG. 1, six insertion holes 4a are respectively provided on the right-hand and left-hand sides of the mounting device body 4. That is, each probe holder 1 has the nine probe mounting parts 2, of which six are inserted into the insertion holes 4a and three are not inserted into the insertion holes 4a. In this way, it is not always necessary for all the probe mounting parts 2 to be inserted into the insertion holes 4a.

The mounting device body 4 is symmetrically provided with lattice-like mark lines 4b serving as positional guides in providing the insertion holes 4a. When providing the insertion holes 4a, by referring to the mark lines 4b, it is possible to provide the insertion holes 4a symmetrically, with the result that the probe holders 1 can be arranged symmetrically. Band-like extension parts 4c, 4d are connected to the right and left ends of the mounting device body 4.

When mounting the probe holders 1 to the head of the subject, the mounting device body 4 is wrapped around the head so as to fit the core 7 in conformity with the forehead, and the end portion of the belt 5b is connected to the main buckle 6. The belts 5a, 5b and the main buckle 6 connect the end portions of the mounting device body 4, and function as a connection adjusting means for adjusting the tightening force in conformity with the size of the head. The tightening force is adjusted to a minimum force needed to fix the mounting device body 4 to the head.

The core 7 is formed of a material having no expandability (a material whose expandability is sufficiently lower than that of the mounting device body 4) so that the core 7 may not impart to the head tightening stronger than the tightening force adjusted by the belts 5a, 5b and the main buckle 6. Variations in the outer peripheral length of the head of the subject are coped with by the belt 5b and the main buckle 6. Further, the mounting device body 4 is equipped with the extension parts 4c, 4d for mounting the probe holder mounting device 3 to the head. By connecting the extension parts 4c, 4d at the back of the head, the probe holder mounting device 3 can be mounted to the head. In this way, by effecting tightening using the extension parts 4c, 4d, it is also possible to mount the probe holder mounting device 3 to the head without using the belts 5a, 5b and the main buckle 6.

The adjusting straps 9a through 9c are thin belt-like straps having a width, for example, of approximately 10 mm, and, when mounting the probe holders 1 to the subject, they are stretched between two different points on the mounting device body 4, and are engaged with the probe holders 1. For example, as shown in FIG. 1, one end portion of the adjusting straps 9a, 9b is connected to the adjusting buckles 8b, 8f, respectively, arranged at symmetrical positions. When mounting the probe holders 1 to the subject, the intermediate portions of the adjusting straps 9a, 9b are engaged with slits 1a, 1b, 1c, 1d, etc. of the probe holders 1, and each of the other end portions of the adjusting straps 9a, 9b are connected to one of the buckles 8a, 8c, 8d, 8f situated on the opposite side of the one end portions. The adjusting straps 9a through 9c are connected to a lateral end of the mounting device body 4 and to the probe holders.

Figure 2:
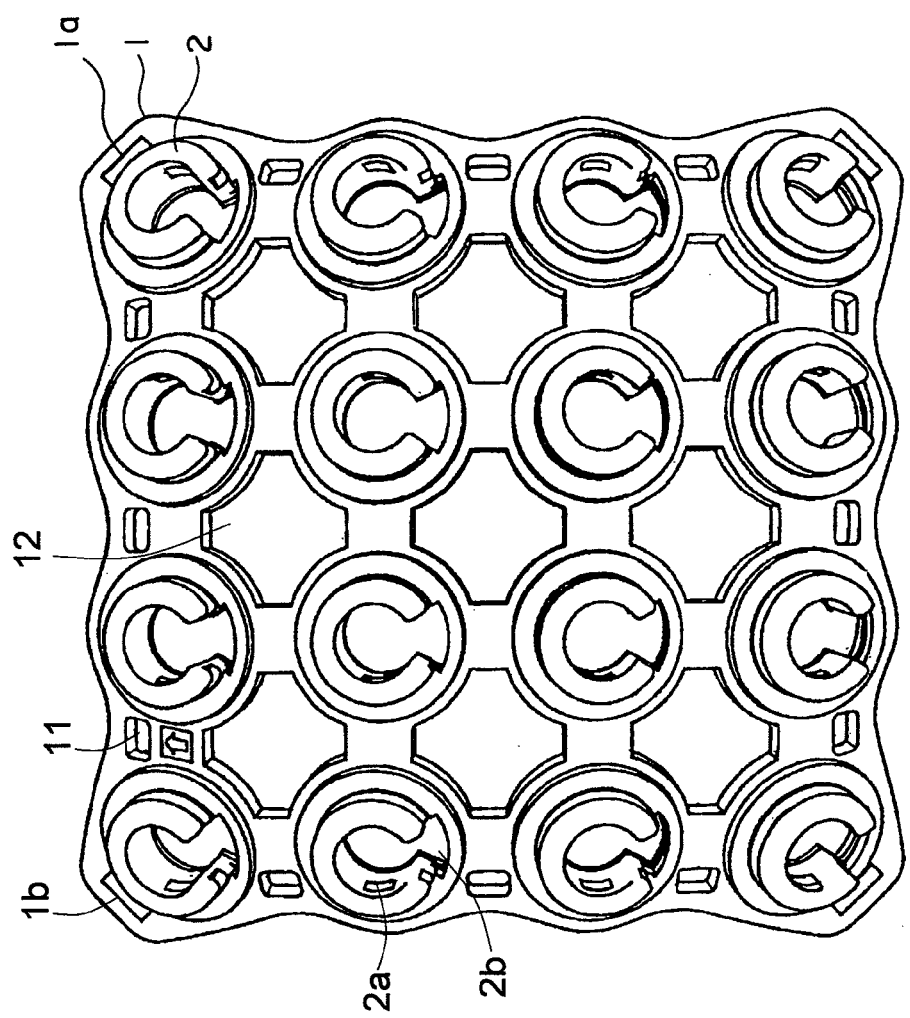
[FIG. 2] A plan view of an example of a probe holder.

FIG. 2 is a plan view of an example of the probe holder with the probe mounting parts 2 being arranged in a 4×4 matrix. The probe holder 1 is formed of a material such as silicone in a bowl-like shape to conform with the configuration of the head of the subject. The probe holder 1 is curved such that the curvature thereof decreases gradually from the central portion toward the peripheral ends thereof. A plurality of rectangular openings 12 are provided in order to facilitate fine adjustment of the probe holder 1 through bending in conformity with the size and configuration of the head of the subject.

At the four corners of the probe holder 1, there are provided the slits 1a, 1b, 1c, 1d, etc. The adjusting strap 9a is passed through the slits 1a, 1b for engagement, and the slits are large enough to allow passage of the adjusting strap 9a.

The probe mounting parts 2 serve to fix optical fiber probes in position. In the probe mounting parts 2, irradiation optical fiber probes and light collection optical fiber probes are alternately arranged. A cutout 2b is provided in a part of the circumference of each probe mounting part 2. That is, each probe mounting part 2 has a C-shaped sectional configuration. Since it is possible to observe the forward end of the mounted probe through the cutout 2b, it is possible to perform setting while checking the way the probe is mounted in relation to the head surface. Further, it is possible to insert a hair avoiding jig, an air blower, or the like into the cutout 2b, making it possible to avoid hair. In the inner peripheral surface of each probe mounting part 2, there is provided a recess 2a for fixing the optical fiber probe in position, and the optical fiber probe is provided with a protrusion adapted to be fitted into the recess 2a. Thus, the optical fiber probe is fixed to the probe mounting part 2 without looseness, keeping a fixed distance between the optical fiber probe and the subject. Further, grooves for locking the mounting device body 4 are provided in the outer peripheral surfaces of the probe mounting parts 2. By locking the mounting device body 4 to those grooves, the mounting device body 4 is fixed to the probe mounting parts 2.

Further, slits 11 are provided at fixed intervals in the outer periphery of the probe holder 1. When fixing the probe holder 1 and the mounting device body 4 to each other through integration, straps or the like are passed through the mounting device body 4 and the slits 11 at the positions where the slits 11 and the mounting device body 4 overlap each other. It is also possible to pass the adjusting strap 9a through the slits 11.

The intermediate portions of the adjusting straps 9a through 9c are engaged with the probe holders 1 by being inserted into the slits 1a. Thus, by adjusting the positions where the adjusting straps 9a through 9c are connected with the adjusting strap buckles 8a through 8f, it is possible to effect fine adjustment of the distance between the probe holders 1 and the distances between the adjusting strap buckles 8a through 8f and the probe holders 1. Further, the probe holders 1 are made to extend in conformity with the configuration of the head, thereby enhancing the intimateness with which the probe holders 1 are held in contact with the head. The adjusting straps 9a through 9c may be passed through other holes of the probe holders 1 or wrapped around the probe mounting parts 2.

Figure 3:
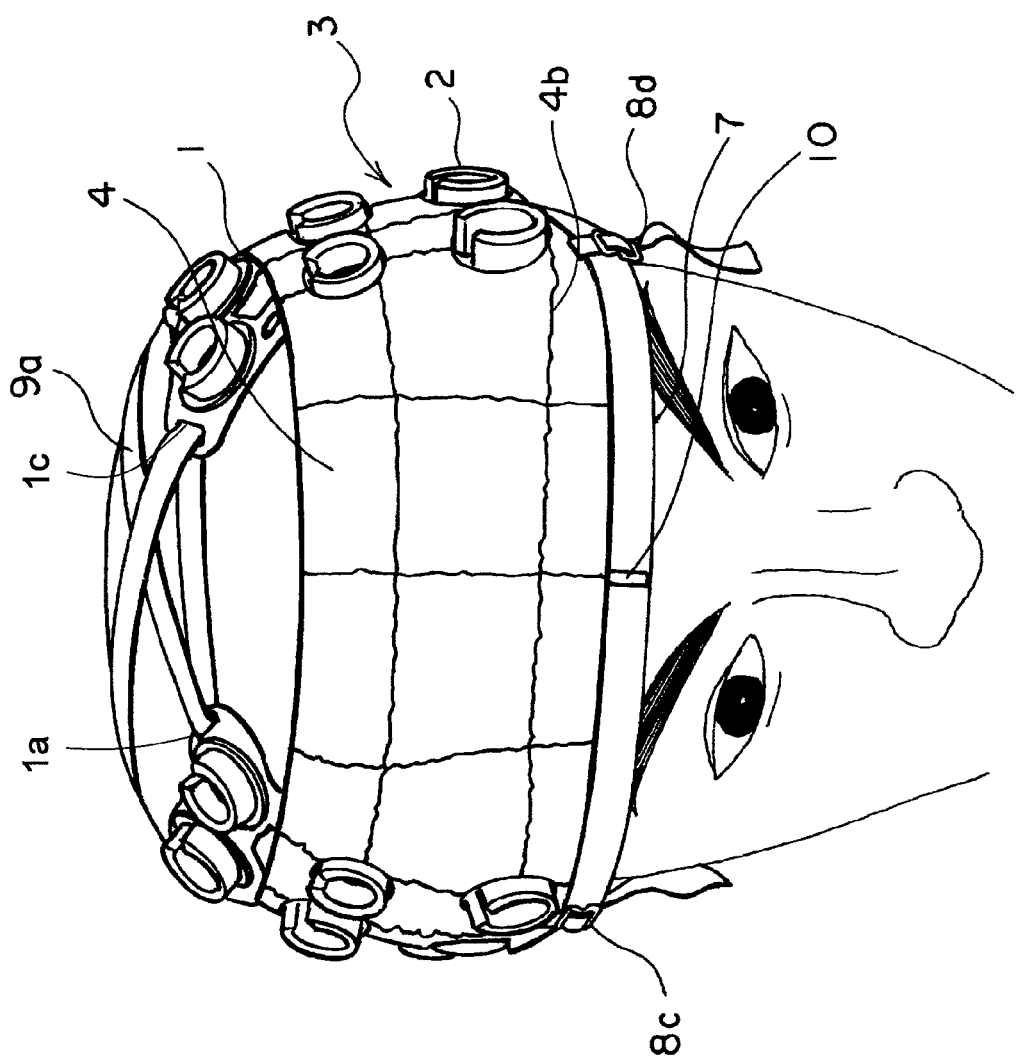
[FIG. 3] A front view of a head of a subject to which the probe holders and the probe holder mounting device of FIG. 1 are mounted.
Figure 4:
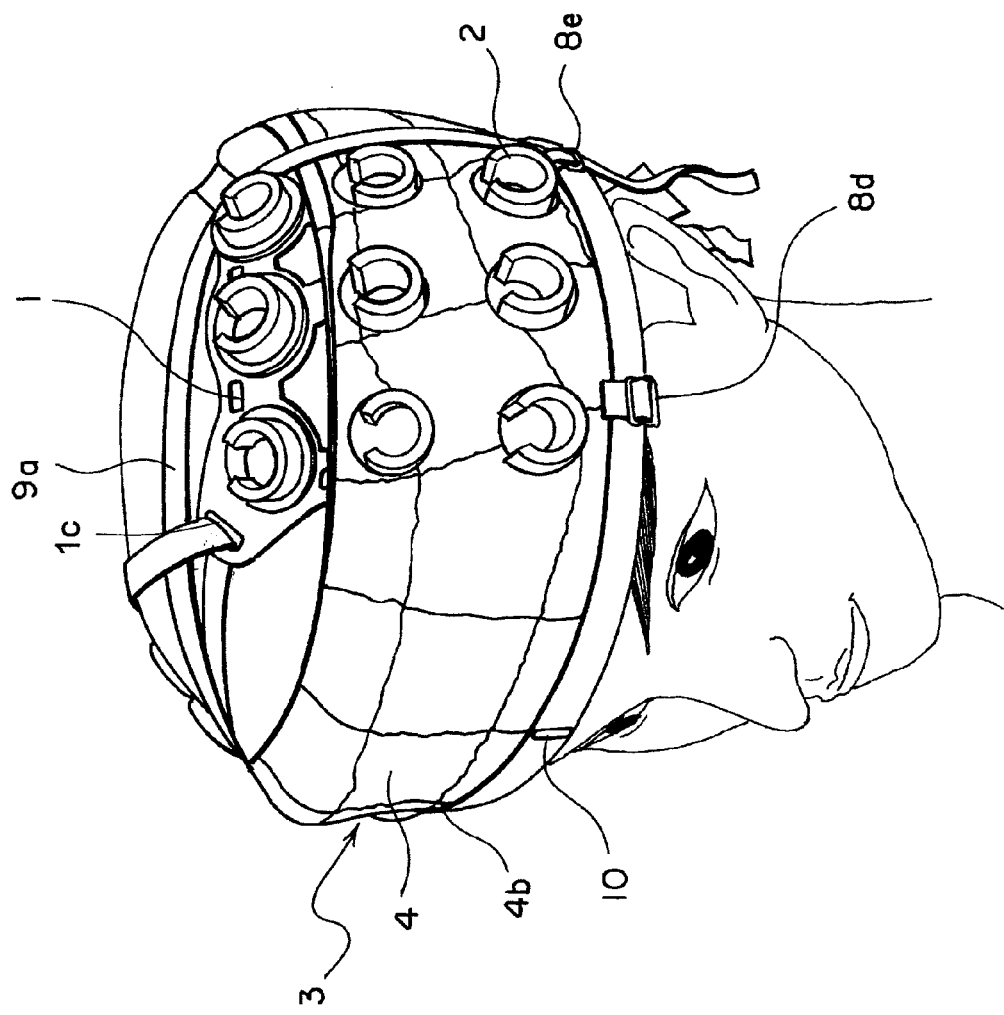
[FIG. 4] A perspective view of the subject of FIG. 3.
Figure 5:
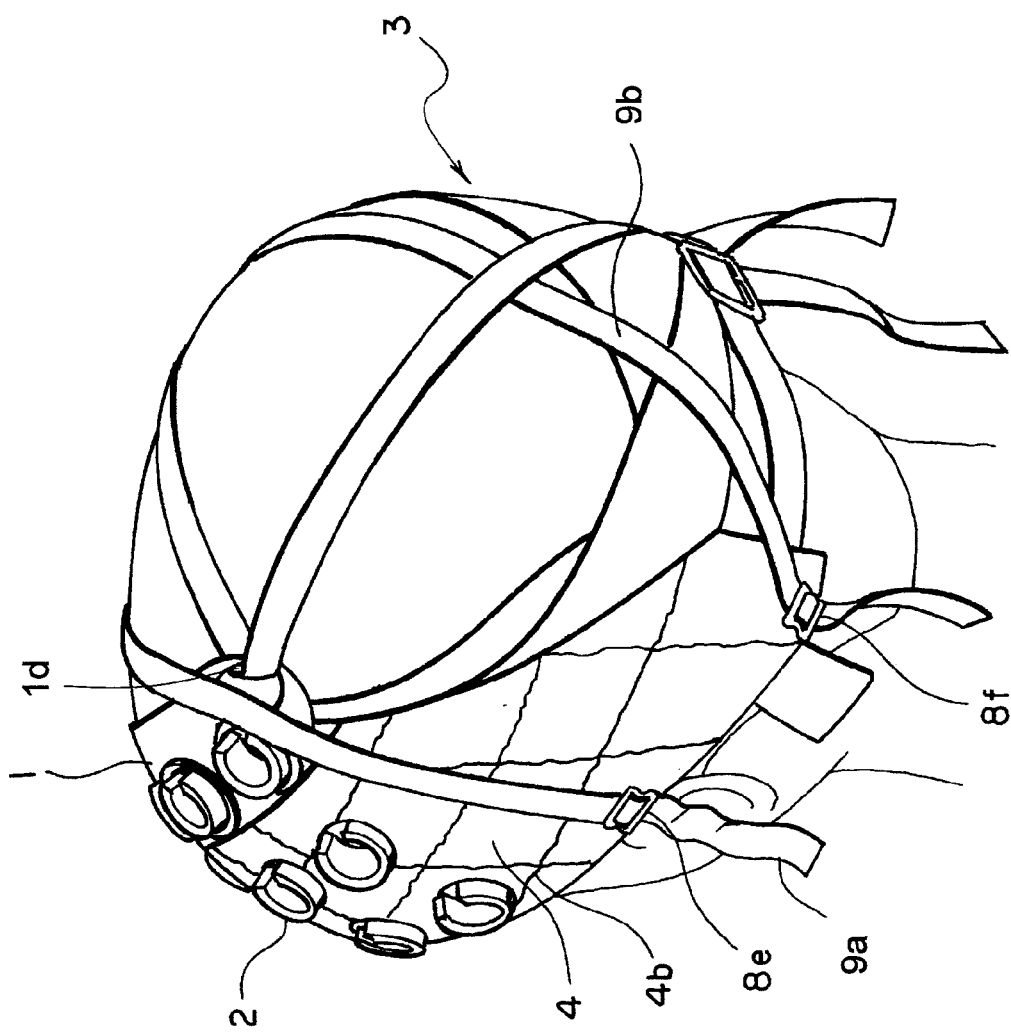
[FIG. 5] A perspective view of the subject of FIG. 3 as seen from an angle different from that of FIG. 4.

FIG. 3 is a front view of the head of the subject to which the probe holders 1 and the probe holder mounting device 3 of FIG. 1 are mounted, FIG. 4 is a perspective view of the subject of FIG. 3, and FIG. 5 is a perspective view of the subject of FIG. 3 as seen from an angle different from that of FIG. 4. There are no particular limitations regarding the arrangement of the adjusting straps 9a, 9b, and the arrangement is determined as appropriate according to the type of probe holders 1 used, the size of the head of the subject, etc.

The connection of the adjusting straps 9a, 9b will be described specifically. The start end portion of the adjusting strap 9a is fixed to the buckle 8b. The adjusting strap 9a fixed to the buckle 8b is passed through the slit 1c on the head-front side of one probe holder 1. Further, the adjusting strap 9a thus passed is passed through the slit 1a on the head-front side of the other probe holder 1. Further, the terminal end portion of the adjusting strap 9a engaged with the two probe holders 1 is fixed with the buckle 8e. Also, the start end portion of the adjusting strap 9b is fixed to the buckle 8f. The adjusting strap 9b fixed to the buckle 8f is passed through the slit 1b on the head-rear side of one probe holder 1. Further, the adjusting strap 9b thus passed is passed through the slit 1d on the head-rear side of the other probe holder 1. Then, the terminal end portion of the adjusting strap 9b engaged with the two probe holders 1 is fixed to the buckle 8a. In this way, the adjusting straps 9a, 9b are tightened.

In this mounting example, the adjusting strap 9c is not used, and thus is removed. Further, the core 7 has a center line 10 indicating the horizontal center of the probe holder mounting device 3. In this way, there are provided not only the mark lines 4b for the positioning of the probe holders 1 with respect to the probe holder mounting device 3, but also a line for the positioning of the probe holder mounting device 3 with respect to the subject, whereby it is possible to arrange the probe holders 1 at the measurement positions more smoothly.

Figure 6:
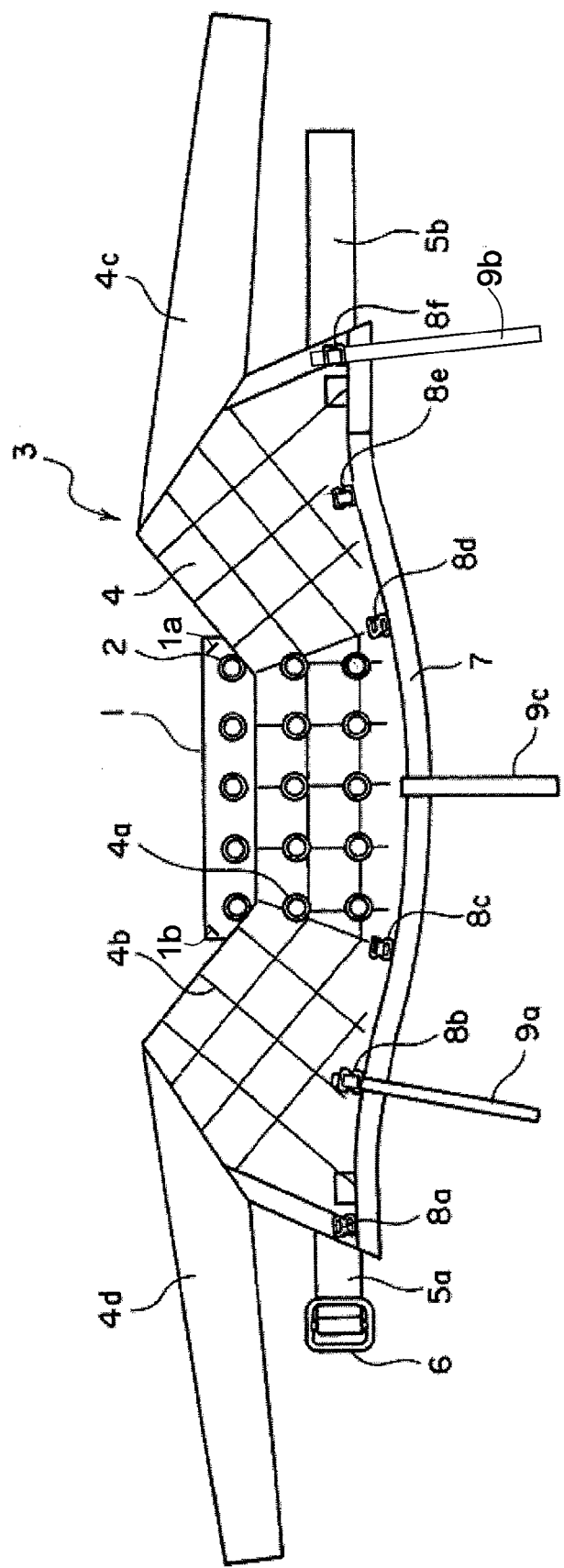
[FIG. 6] A plan view of the probe holder mounting device of FIG. 1 as combined with a different type of probe holder.

FIG. 6 is a plan view of the probe holder mounting device 3 of FIG. 1 as combined with the probe holder 1 of a different type. In this example, the probe mounting parts 2 are arranged in a 5×3 matrix, with the probe holder 1 being arranged at the center of the probe holder mounting device 3. That is, FIG. 1 shows an arrangement of the probe holders 1 for performing measurement on the right and left temporal portions, and FIG. 6 shows an arrangement of the probe holder 1 for performing measurement on the frontal portion. That is, the mounting device body 4 has a front mounting portion to be held on the frontal portion of the subject, a left-hand mounting portion to be held on the left temporal portion, and a right-hand mounting portion to be held on the right temporal portion. Thus, the probe holder mounting device 3 is applicable to all types of probe holders 1 and applicable to all measurement positions.

In the probe holder mounting device 3, which uses the band-like mounting device body 4 to be wrapped around the subject, there is less of an intense tightening feel for the subject as compared with the case of a constrictive cap-type mounting device, of annular rubber member or the like. Further, the top portion of the head is not covered with the mounting device body 4 but exposed, so the mounting position can be easily checked, and the mounting on the subject is facilitated. Further, through connecting position adjustment of the adjusting straps 9a through 9c, it is possible to effect fine adjustment on the position of the probe holder 1.

Further, the mounting device body 4 is provided with the core 7 having no expandability, and, when wrapping the mounting device body 4 around the head of the subject, the core 7 is applied to the forehead of the subject so as to be in conformity with the configuration thereof, so it is possible to fix the mounting device body 4 firmly to the subject without causing the subject to experience an intense tightening feel.

Further, since the mounting device body 4 is provided with the mark lines 4b, it is possible to provide the insertion holes 4a symmetrically, making it possible to arrange the probe holders 1 easily at the proper positions.

As the expandable cloth forming the mounting device body 4, a nonwoven fabric of polyester fibers, polyolefin fibers or the like is suitable.

Further, it is also possible to provide the belt 5b with a scale in correspondence with the size of the head of the subject, using the scale as a guide in adjusting the tightening degree.

Further, while there are no particular limitations regarding the color of the mounting device body 4, at least the portions where the probe holders 1 are mounted are preferably formed in black, which helps to achieve an improvement in terms of shielding property.

Further, by making the color of the portions of the mounting device body 4 where the probe holders 1 are mounted different from the color of at least one of the belts 5a, 5b, the adjusting straps 9a through 9c, and the extension parts 4c, 4d, it is possible to improve the workability of the mounting operation to the head of the subject.

Further, it is also possible to provide a scale on the surface of the core 7. When mounting the mounting device body 4 and the probe holders 1, a scale in correspondence with the positions of the eyebrows and the glabella is recorded, whereby it is possible to repeatedly mount the mounting device body 4 and the probe holders 1 while checking the positions of the eyebrows and the glabella in accordance with the previously recorded scale. Thus, it is possible to achieve an improvement in terms of the reproducibility of the mounting of the mounting device body 4 and the probe holders 1 to the head.

The invention claimed is:

1. A probe holder mounting device for a biological photometric device, comprising:
a probe holder having a plurality of probe mounting parts to which optical fiber probes are mounted;
a band-like mounting device body having a plurality of insertion holes into which the plurality of probe mounting parts are to be inserted to fix the probe holder in position by means of the plurality of insertion holes, and having a connection part among the plurality of the probe mounting parts;
belts whose one ends are respectively connected to both longitudinal ends of the band-like mounting device body and whose other ends are engaged with each other; and
an adjusting belt connected to the band-like mounting device body at a position where the probe holder is fixed in position in a lateral direction of the band-like mounting device body,
wherein the plurality of the probe mounting parts and the connection part are symmetrically provided with mark line serving as positional guides in providing the plurality of the insertion holes.

2. The probe holder mounting device for a biological photometric device according to claim 1, wherein the adjusting belt comprises a plurality of adjusting belts provided on the band-like mounting device body.

3. The probe holder mounting device for a biological photometric device according to claim 2, further comprising a plurality of adjusting belt fastening members which are mounted at intervals to a lateral end of the band-like mounting device body and to which the adjusting belts are connected.

4. The probe holder mounting device for a biological photometric device according to claim 2, wherein the probe holder is provided at an end thereof with a slit through which the adjusting belt is to be passed.

5. The probe holder mounting device for a biological photometric device according to claim 2, wherein the adjusting belt is directly connected to the band-like mounting device body.

6. The probe holder mounting device for a biological photometric device according to claim 1, further comprising a core which is provided on the band-like mounting device body, which is formed of a material of lower expandability than the band-like mounting device body, and which is held snugly on the forehead of a subject when wrapping the mounting device body around the head of the subject.

7. The probe holder mounting device for a biological photometric device according to claim 6, wherein the core is provided with a center line indicating a horizontal center thereof.

8. The probe holder mounting device for a biological photometric device according to claim 1, wherein the mark lines are provided in a lattice-like fashion.

9. The probe holder mounting device for a biological photometric device according to claim 1, wherein the band-like mounting device body has a front mounting portion to be held on a frontal portion of a subject, a left-hand mounting portion to be held on a left temporal portion of the subject, and a right-hand mounting portion to be held on a right temporal portion of the subject.

10. The probe holder mounting device for a biological photometric device according to claim 1, wherein the band-like mounting device body is provided with band-like extension parts connected to left and right end portions thereof.

11. The probe holder mounting device for a biological photometric device according to claim 1, further comprising a second belt connected to both ends of the band-like mounting device body.

12. The probe holder mounting device for a biological photometric device according to claim 1, wherein the probe holder comprises a plurality of probe holders fixed to the band-like mounting device body.

13. The probe holder mounting device for a biological photometric device according to claim 1, wherein the plurality of probe mounting parts are arranged in a matrix-like fashion.

14. The probe holder mounting device for a biological photometric device according to claim 1, wherein the band-like mounting device body is formed of an expandable cloth.

15. The probe holder mounting device for a biological photometric device according to claim 1, wherein the adjusting belt is connected to a lateral end of the band-like mounting device body and to the probe holder.

16. The probe holder mounting device for a biological photometric device according to claim 1, wherein the probe holder is formed of silicone in a bowl-like configuration and is provided with a rectangular opening.

17. The probe holder mounting device for a biological photometric device according to claim 1, wherein the probe holder is curved such that the curvature thereof is gradually diminished from a central portion thereof toward a peripheral end thereof.

18. A probe holder mounting device for a biological photometric device comprising:
a probe holder having a plurality of probe mounting parts to which optical fiber probes are mounted;
a band-like mounting device body having a plurality of insertion holes into which the plurality of probe mounting parts is to be inserted to fix the probe holder in position by means of the plurality of the insertion holes;
a first connection part having the plurality of probe mounting parts as one part;
belts whose one ends are respectively connected to both longitudinal ends of the band-like mounting device body and whose other ends are engaged with each other;
an adjusting belt connected to the band-like mounting device body at a position where the probe holder is fixed in position in a lateral direction of the band-like mounting device body; and
a second connection part connected to the first connection part and the belt,
wherein the first connection part and the second connection parts are symmetrically provided with mark lines serving as positional guides in providing the plurality of the insertion holes.

* * * * *